United States Patent
Frey et al.

(10) Patent No.: US 9,271,645 B2
(45) Date of Patent: Mar. 1, 2016

(54) SYSTEM AND METHOD OF SCAN CONTROLLED ILLUMINATION OF STRUCTURES WITHIN AN EYE

(71) Applicant: LensAR, Inc., Orlando, FL (US)

(72) Inventors: Rudolph W. Frey, Winter Park, FL (US); Richard Ty Olmstead, Ovideo, FL (US); Gary P. Gray, Orlando, FL (US); Steven E. Bott, Oviedo, FL (US); James Strobel, Titusville, FL (US)

(73) Assignee: LENSAR, LLC., Orlando, FL (US)

( * ) Notice: Subject to any disclaimer, the term of this patent is extended or adjusted under 35 U.S.C. 154(b) by 0 days.

(21) Appl. No.: 14/335,187

(22) Filed: Jul. 18, 2014

(65) Prior Publication Data

US 2015/0022779 A1    Jan. 22, 2015

Related U.S. Application Data

(63) Continuation of application No. 13/273,653, filed on Oct. 14, 2011, now Pat. No. 8,801,186.

(60) Provisional application No. 61/455,178, filed on Oct. 15, 2010.

(51) Int. Cl.
| | |
|---|---|
| *A61B 3/10* | (2006.01) |
| *A61B 3/14* | (2006.01) |
| *A61B 3/08* | (2006.01) |
| *A61B 3/107* | (2006.01) |
| *A61B 3/117* | (2006.01) |
| *A61B 3/00* | (2006.01) |

(52) U.S. Cl.
CPC ............ *A61B 3/1025* (2013.01); *A61B 3/0025* (2013.01); *A61B 3/08* (2013.01); *A61B 3/107* (2013.01); *A61B 3/1173* (2013.01); *A61B 3/14* (2013.01)

(58) Field of Classification Search
CPC ..... A61B 3/0008; A61B 3/107; A61B 3/1173
USPC .......................... 351/205, 210, 212, 221, 246
See application file for complete search history.

(56) References Cited

U.S. PATENT DOCUMENTS

| | | | |
|---|---|---|---|
| 8,801,186 B2 * | 8/2014 | Frey et al. ...................... 351/221 |
| 2010/0004641 A1 * | 1/2010 | Frey et al. .......................... 606/4 |
| 2012/0089134 A1 * | 4/2012 | Horvath et al. .................... 606/6 |

* cited by examiner

*Primary Examiner* — Huy K Mai
(74) *Attorney, Agent, or Firm* — Glen P. Belvis; Steptoe & Johnson

(57) ABSTRACT

There is provided a system, apparatus and methods for enhancing the illumination of structures of the eye using predetermined scan patterns of an illuminating light beam. The systems, apparatus and methods further provide for obtaining enhanced single images of multiple structures of the eye.

12 Claims, 8 Drawing Sheets

SYSTEM AND METHOD OF SCAN CONTROLLED ILLUMINATION OF STRUCTURES WITHIN AN EYE

This application is a continuation of U.S. patent application Ser. No. 13/273,653, filed on Oct. 14, 2011, now pending, which claims the benefit of priority under 35 U.S.C. §119(e)(1) of U.S. Provisional Application Ser. No. 61/455,178, filed Oct. 15, 2010, the entire contents of each of the above mentioned U.S. regular and provisional applications are incorporated herein by reference.

BACKGROUND OF THE INVENTION

1. Field of the Invention

The present inventions relate to methods and systems for illuminating, obtaining images of, and determining the shape and position of structures within an eye, and in particular, the cornea, natural human crystalline lens and adjacent structures of the eye. More particularly, the present inventions relate to variably controlled scanning of laser light illumination of such structures, controlled and predetermined digital capture of the images of the illuminated structures with an accurately calibrated digital camera and the creation of enhanced digital composite images of the illuminated structures.

2. Description of the Related Art

Presbyopia most often presents as a near vision deficiency, the inability to read small print, especially in dim lighting after about 40-45 years of age. Presbyopia, or the loss of accommodative amplitude with age, relates to the eye's inability to change the shape of the natural crystalline lens, which allows a person to change focus between far and near, and occurs in essentially 100% of the population. Accommodative amplitude has been shown to decline with age steadily through the fifth decade of life.

Cataracts, or the condition when the natural crystalline lens becomes opaque and clouds vision, occurs in millions of people per year and are treated effectively with surgical techniques, such as ultrasonic phacoemulsification pioneered by Kelman 30 years ago. Although the techniques have been refined over the years, safety concerns from ocular trauma, especially to the corneal endothelium from the ultrasonic energy required to break up a hardened cataract, is undesirable; especially for those with a compromised corneal endothelium, such as those with Fuchs Dystrophy. Moreover, the use of lasers in the treatment of cataracts has a further issue. Cataracts scatter light, including laser light, and thus, can prevent a laser treatment beam from having the desired tissue effect. Moreover, the light scattering effect of cataracts and other opacifications can make optically determining the position and shape of the lens difficult.

The established treatment for cataracts is the removal of the opacified human crystalline lens and its replacement with an intraocular lens ("IOL"). In general, IOLs include a small plastic lens with plastic side struts, called haptics, to hold the lens in place within the capsular bag inside the eye. Exemplary types of IOLs include monofocal lenses, multifocal IOLs which provide the patient with multiple-focused vision at far and reading distance, and accommodative IOLs which provide the patient with visual accommodation. The flexible nature of many IOLs enables them to be rolled and/or folded up for insertion into the lens capsule.

The removal of the opacified natural crystalline lens and replacement with a lens replacement material, such as an IOL, presently employs a capsulorhexis and/or a capsulotomy procedure. A capsulorhexis generally includes of the removal of a part of the anterior lens capsule and the creation of a hole or opening in the lens capsule, which results, at least in part, from a tearing action. A capsulotomy generally includes of a cutting of the lens capsule, without or with minimum tearing of the lens capsule. Thus, to remove the opacified natural lens material, the lens capsule is opened. There are several known techniques for performing a capsulorhexis and a capsulotomy, including the use of a Fugo plasma blade.

Recently laser systems and methods for treating of cataracts, presbyopia, performing capsulotomies, and for the sectioning and removal of natural crystalline lens material have been developed and introduced. Examples of such innovative and novel systems and methods are found in commonly assigned published patent applications US 2007/0173794, US 2007/0173795, US 2007/0185475, US 2010/0004641, US 2010/0004643, US 2010/0022994, US 2010/002995, US 2010/0042079, WO 2007/084627, and WO 2007/084694, the entire disclosures of each of which are incorporated herein by reference. Further examples of such innovative and novel systems and methods are found in commonly assigned U.S. patent application Ser. Nos. 12/840,818, 12/831,859, 12/831,845, 12/831,783 and 12/842,870, the entire disclosures of each of which are incorporated herein by reference.

In the treatment of cataracts, presbyopia, conditions of the eye, and afflictions of the eye, and in particular, in using lasers for such treatments, the determination of the position (relative to other structures of the eye and/or relative to any treatment equipment, such as a laser), and the shape of the structures of the eye is essential to allow the precise application of laser energy to effect the treatment. In general, greater accuracy and precision in making such determinations is beneficial. Further, visual images of these structures for the treating physician to observe can be beneficial and can enhance the outcome of any procedures. Accordingly, as provided in detail in this specification, improvements in the illumination of structures of the eye are provided herein, which improvements give rise to improved determination of the position and shape of structures within the eye, as well as, enhanced images of those structures.

SUMMARY

It is desirable to have systems and methods that would provide enhanced images of the structures of the eye and that would provide for the position and shape of those structures. The present invention, among other things, solves these needs by providing controlled light beam illumination of such structures. Thus, there is provided herein systems and methods for the enhanced illumination of the structures of the eye and for the capture of single composite images of those structures having optimal illumination for each structure.

It is further desirable that the image capture device be well calibrated to permit dimensionally accurate images of the structures of the eye. Such calibration is desirable to eliminate sources of image distortion such as the tilt between the angle of illumination beam and the image plane of the image capture device used to form composite images of the structures of the eye or optical aberrations in the image capture device. Such sources of image distortion are common in imaging applications requiring a large depth of field, such as the present application in imaging the structures of the eye.

Thus, there is provided a method for enhancing the illumination of components of a multi-component structure, the method including: selecting a first predetermined illumination light scan pattern, having a predetermined rate and scan region; selecting a second predetermined illumination light scan pattern, having a predetermined rate and scan region;

wherein, at least one of the second scan rate or area is different from the first scan rate or scan region; directing an illuminating light beam in the first scan pattern toward a first component of the multi-component structure, whereby a first illuminated image is created; directing an illuminating light beam in the second scan pattern toward a second component of the multi-component structure, whereby a second illumination image is created; digitally capturing the first illumination image on a first predetermined portion of an image capture device; digitally capturing the second illumination image on a second predetermined portion of the image capture device, wherein the second portion is different than the first portion; thus a single composite image of the illuminated components is created by the image capture device without need for registration of the first to the second illumination image.

There is further provided the forgoing method in which at least one of the predetermined illumination light scan patterns is optimized for the component to be scanned; the first component is the cornea of an eye; the first component is the natural crystalline lens of any eye; and/or the second component is the natural crystalline lens of the eye.

There is further provided a method to calibrate the image capture device so that there exists a known relationship or mapping between each point in the three dimensional volume of space containing the components of interest in the eye and the two dimensional image plane of the image capture device. The method includes a means to present one or more calibration targets to the image capture device, before (or after) use of the image capture device to generate images of structures in the eye, such calibration targets together include a three dimensional array or series of a plurality of uniquely identifiable objects with known positions in the volume of space in which the eye will be imaged. The method further includes means to capture one or more images of the calibration target(s) with the image capture device and identify some or all of the uniquely identifiable objects in the captured image(s) and to record the positions, within the captured image(s), of some or all of the uniquely identifiable objects. Further, the method includes a means to determine a linear or non-linear mathematical relationship or mapping between the known positions of the uniquely identifiable objects in the calibration target(s) and the recorded positions of the uniquely identifiable objects in the captured image(s). Still further, the method includes means to use the foregoing mapping to reduce or eliminate sources of image distortion in the image capture device or inherent in the geometrical arrangement of the image capture device with respect to the volume of space in which the object to be imaged, for example, structures within the eye or calibration target(s) and so be generate an image which is substantially dimensionally accurate. By dimensionally accurate is meant that the distances between entities, such as eye structures or parts of eye structures, in the image captured by the image capture device are substantially the same as corresponding distances between the same entities in the actual object being imaged, except for a single overall scale factor.

Yet further, there is provided a system for providing enhanced illumination of the components of a multi-component structure, the system having: an illumination source for providing an illumination beam; a scanner optically associated with the illumination light source for scanning the illumination beam; a control system, associated with the light source and scanner; the control system including: a first predetermined illumination beam scan pattern, having a predetermined rate and scan region; a second predetermined illumination scan pattern, having a predetermined rate and scan region; wherein, at least one of the second scan rate or region is different from the first scan rate or region; means for digitally capturing a first image generated by the first illuminating beam scan pattern; means for digitally capturing a second image generated by the second illuminating laser beam scan pattern; and, the means for digitally capturing the first image and the means for capturing the second image being different portions of the same means.

Additionally, there is provided a system for the enhanced illumination of the structures of the eye, the system having: an illumination source for providing an illumination beam; a scanner optically associated with the illumination source for scanning the illumination beam; a control system, associated with the illumination source and scanner; the control system including: a first predetermined illumination scan pattern, having a predetermined rate and scan region; a second predetermined illumination scan pattern, having a predetermined rate and scan region; wherein, at least one of the second scan rate or region is different from the first scan rate or area; region for digitally capturing a first image generated by the first illuminating beam scan pattern; means for digitally capturing a second image generated by the second illuminating beam scan pattern; and the means for digitally capturing the first image and the means for capturing the second image being different portions of the same means.

Yet further there is provided a method for enhancing the illumination of the structures of the eye, the method including: scanning an illumination beam in a predetermined rate and scan region over an area of a cornea of an eye; and, scanning the illumination beam at a predetermined rate and area over an area of a lens of the eye; wherein the illumination of the cornea is different from the illumination of the lens. This method may further be such that the illumination of the cornea and the lens are respectively optimal.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE DRAWINGS AND THE PREFERRED EMBODIMENTS

Figure 1A:
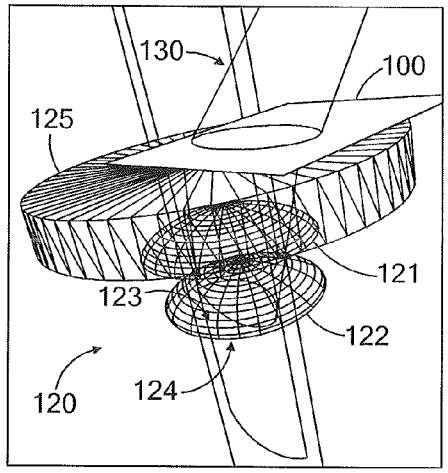
FIGS. 1A to 1D are four different perspective illustrations of the same laser scanning illumination of the structures of the eye of the present invention.
Figure 1B:
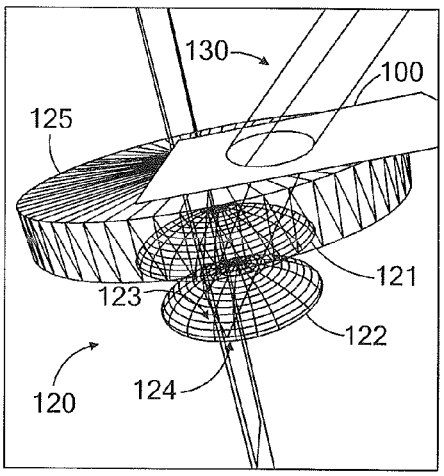
Figure 1C:
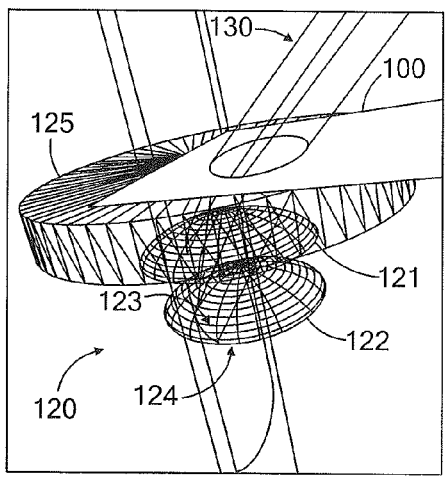
Figure 1D:
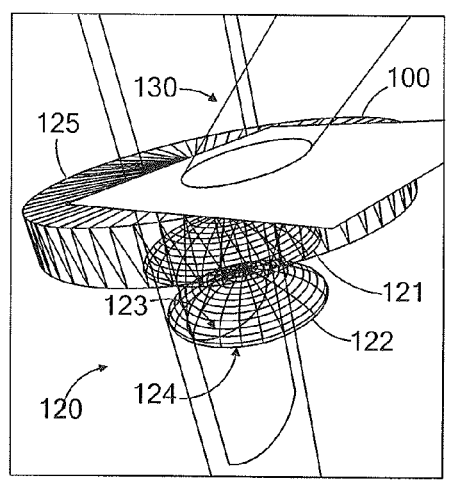

In general, the present inventions relates to methods and systems for providing enhanced laser scan illumination of the eye to provide for improved images of the structures of the eye, and in particular, the cornea and the natural crystalline lens. The present invention further relates to systems and methods utilizing the enhanced laser scan illumination for determining the shape and position of the cornea and the lens and to provide enhanced images of those structures.

In general, the present invention uses a light beam and scanner to illuminate the structures of the eye. The light beam can be generated by a non-coherent light source or a laser source. Examples of laser beam and scanner systems that can be used for illumination are disclosed in US 2007/0173794, US 2007/0173795, US 2007/0185475, US 2010/0004641, US 2010/0004643, US 2010/0022994, US 2010/002995, US 2010/0042079, WO 2007/084627, and WO 2007/084694. Further examples of such laser beam and scanner systems are found in commonly assigned U.S. patent application Ser. Nos. 12/840,818, 12/831,859, 12/831,845, 12/831,783 and 12/842,870. In the case of using a laser source, the illumination laser should be an eye safe laser. Thus, the illumination laser could be a laser that is deferent from the therapeutic laser, or it could be the therapeutic laser, but at a power level that is below the threshold where the laser can affect the structures that are illuminated. In the case of using a non-coherent light source, the laser beam and scanner systems disclosed in the previously mentioned US 2007/0173794, US 2007/0173795, US 2007/0185475, US 2010/0004641, US 2010/0004643, US 2010/0022994, US 2010/002995, US 2010/0042079, WO 2007/084627, WO 2007/084694, U.S. patent application Ser. Nos. 12/840,818, 12/831,859, 12/831, 845, 12/831,783 and 12/842,870 can be adapted to include such a non-coherent light source for illumination instead of a laser source.

In conventional illumination techniques, which illuminate all of the structures at once and capture an image of these illuminated structures for example with a digital camera; the images of the eye are over or under exposed in different areas and on different structures. Thus, with these conventional techniques it is believed that in general evenly illuminated clear and sharp images of multiple structures of the eye, in a single image, are difficult to obtain, if not unobtainable. Instead, such conventional images have over exposed or underexposed areas resulting in bright and dark spots that detrimentally affect the clarity and sharpness of the overall image. These detrimental effects are in part due to the different structures of the eye responding differently to the illumination light. Thus, illumination light that is best to capture, for example, an image of the anterior surface of the lens, may not be best to capture a peripheral edge of the cornea. However, in such "one illumination source fits" all type of techniques there no way, or at a minimum it is exceeding difficult, to tailor the illumination to all of the structures of the eye in a single image.

To solve these drawbacks of conventional illumination and image capture systems, the present inventions scan an illumination beam of light on the structures of the eye to be illuminated. The scan rate and scan area are predetermined based upon the structure of the eye to be illuminated, the section of that structure to be illuminated, and the relative location and size of the pupil. As the illumination beam of light is scanned along a section of a particular structure of the eye to be illuminated, the illuminated images from that scan are captured by predetermined pixels, or lines, on an image capture device, such as a digital camera. As additional structures in the eye are scanned, other predetermined pixels, or lines on the digital camera capture their illuminated images. In this way, a composite image, based upon each individual scan of each individual structure, of the illuminated structures of the eye is built, with each structure having the optimal illumination. Thus, the present system provides the ability to have predetermined and preselected multiple and varied illuminations of components parts, sub-structures, or structures of a multi-component structure, such as the human eye, and to create a single, clear and sharp image of all of those components in the multi-component structure. The images can be created real-time in a single procedure (serial collection of a plurality of illumination scans) without the need for subsequent or later digital alteration or digital enhancement of the images, such as by using software sold under the trademark PHOTOSHOP. Thus, for example in the present system and method the size of the pupil is determined. The scanning of light on a particular area of the cornea is performed. The scan preferably is from about 12-13 mm in length and at a rate that properly, and preferably optimally, illuminates the cornea based upon the setting of the camera. The illuminated images from this first scan would be for example captured by pixels at for example lines X to X+250 of the camera. The scan of a particular area of the anterior surface of the lens of the eye would then be performed (preferably the areas are directly anterior to the area of the cornea and thus a cross-section of the structures is obtained). To avoid interference from the pupil, this scan is from about 7 to 7.5 mm and at a rate that properly, and preferably optimally, illuminates the anterior capsule of the lens based upon the setting of the camera. The illuminated images for this second scan would be for example captured by pixels at for example lines X+252 to X+300. In this way both the scanned images of the cornea and the anterior capsule of the lens would be captured in a single image, with each having different and optimal illumination. The steps of scanning, and capturing images on further lines of the camera would be continued until all of the desired structures of the eye have been captured in a single image. Further, it should be understood, that the order of scans and the location of capture on the lines of the camera may vary for different applications. In addition, the light beam used in the scan can be generated by a laser or by a super luminescent diode (SLD). Use of an SLD is beneficial in that it is a non-coherent source that avoids laser speckle which degrades the image quality.

Turning to FIGS. 1A to 1D, there are four views from different perspectives of the images of scans of the illuminating light to create single composite images 100 of areas of the structures of the eye 120. Thus, in these figures there is shown a cornea 121 and a natural crystalline lens 122, which has an anterior capsule 123 and a posterior capsule 124. There is also shown an image window 125, which may be of the illumination system, such as a part of a patient interface. In these figures there are shown ray lines 130 signifying the scanned illumination light beam used to illuminate the structures of the eye. As can be seen from the image position 100, these figures show different perspective views of the same scans, image, and eye structures, but from different views (e.g., 12, 3, 6 and 9 o'clock if one were to use the face of a clock as a reference).

Figure 2:
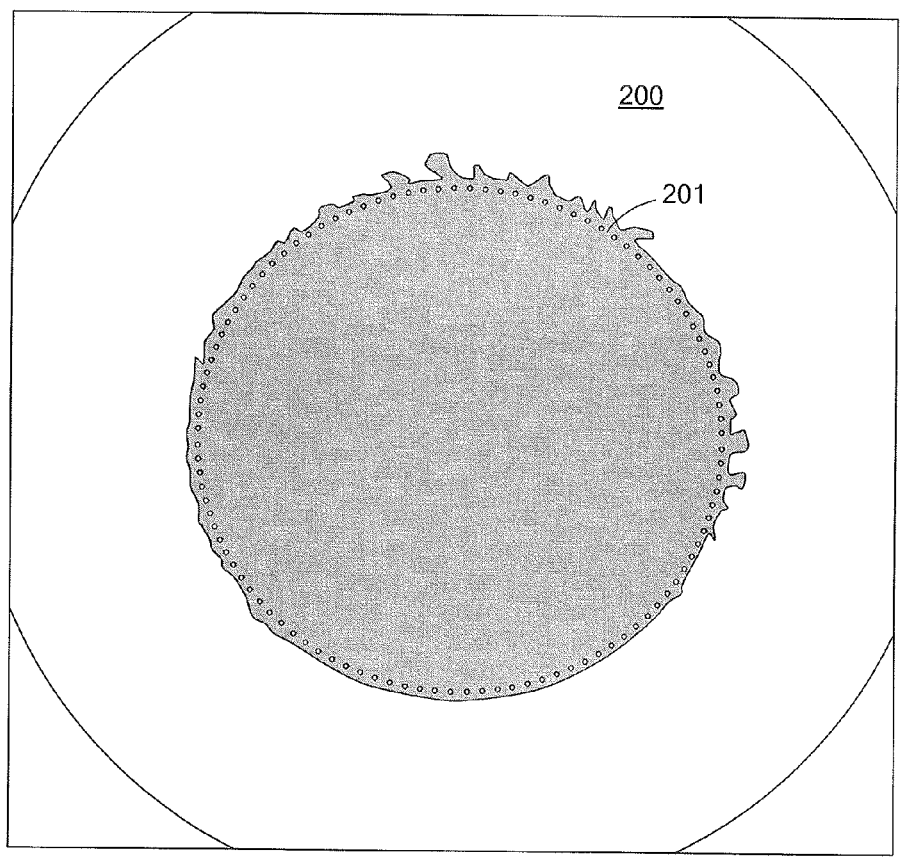
FIG. 2 is a diagram of a pupil of an eye.

FIG. 2 shows a section of an eye 200, with a computer generated line 201 positioned concentrically with the edge of the pupil. This line 201 can be used to determine the diameter of the dilated pupil, which diameter may then be used to determine and optimize the length of a particular illumination scan of structures that are positioned posterior to the pupil.

Figure 3:
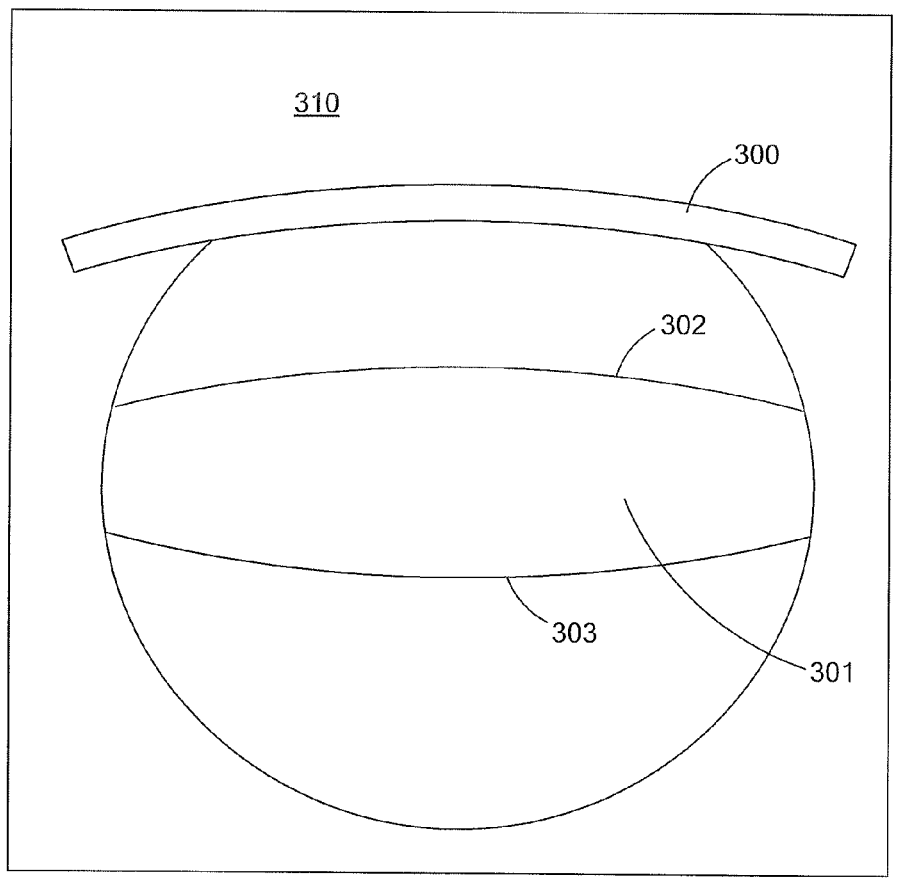
FIGS. 3 to 5 are single composite images of the eye obtained by the present invention.
Figure 4:
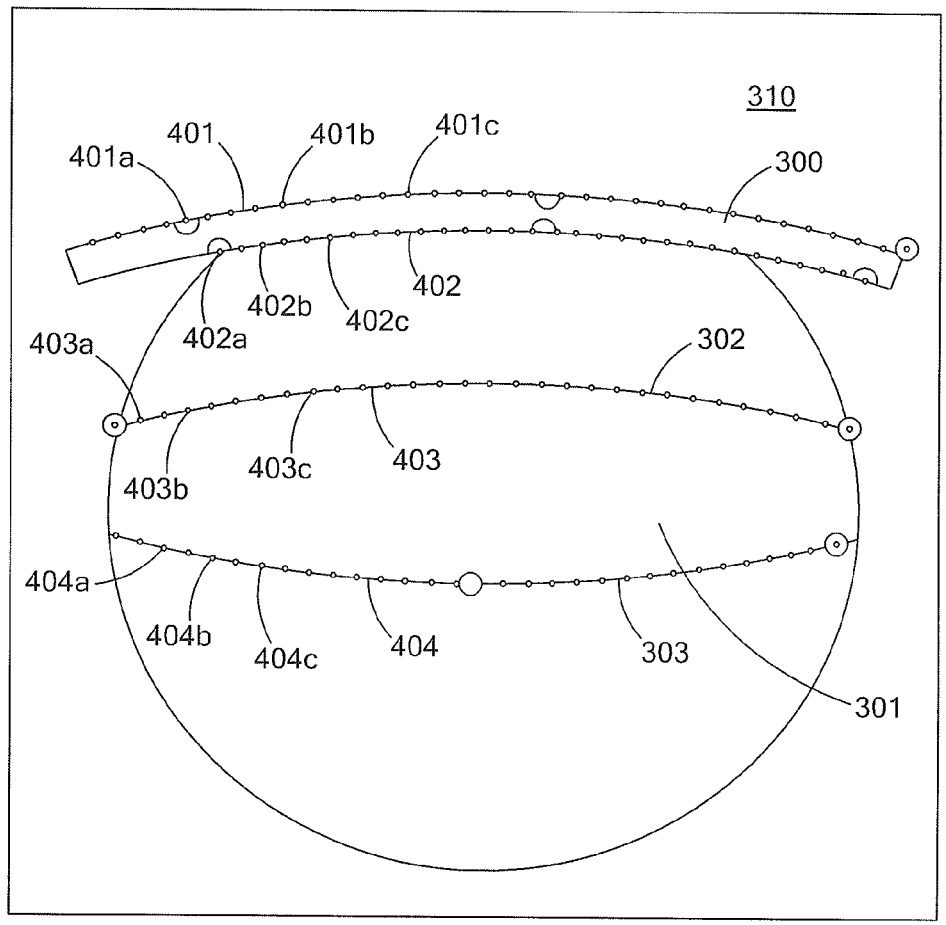
Figure 5:
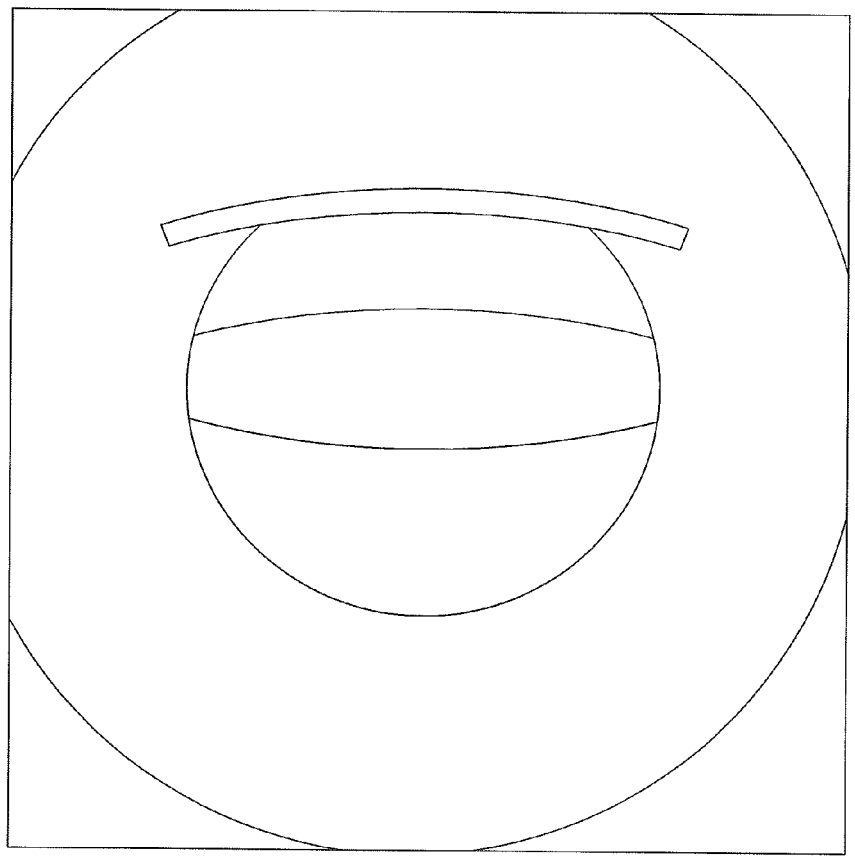
Figure 6:
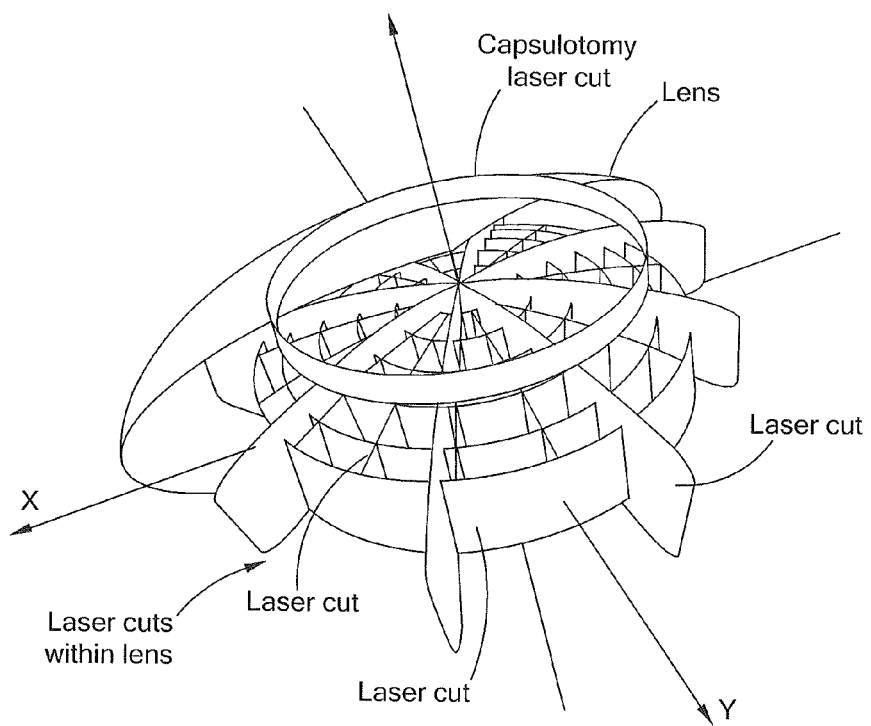
FIG. 6 is an illustration of a therapeutic laser shot pattern that can be directed toward the eye based upon the enhanced images obtained by the present inventions.

FIG. 3 provides a single image 310 of the structures of the eye that was taken using scanned light illumination, which each scan having a different scan rate and scan area, which rates and areas were predetermined to optimize the images obtained. Thus, there is shown the cornea 300, the lens 301, and the lens anterior capful 302 and posterior capsule 303. Turning to FIG. 4 there is shown the same image 310 of FIG. 3 to which position and shape determination lines have been added via computer. Thus, line 401 follows the anterior surface of the cornea and has a plurality of points, of which points 401a, 401b and 401c are numbered for purposes of illustration and simplification of the drawing. Line 402 follows the posterior surface of the cornea and has a plurality of points, of which points 402a, 402b and 402c are numbered for purposes of illustration and simplification of the drawing. Line 403 follows the anterior lens capsule and has a plurality of points, of which points 403a, 403b and 403c are numbered for purposes of illustration and simplification of the drawing. Line 404 follows the posterior lens capsule and has a plurality of points, of which points 404a, 404b and 404c are numbered for purposes of illustration and simplification of the drawing. These various computer generated points and lines, which are generated based upon the enhanced image obtained from the light scan illumination, are used to determine the position and shape of the lens and cornea. This position and shape information can then be used to determine a shot pattern for the therapeutic laser such as the shot patterns shown in FIG. 6.

The scanned illumination techniques have the ability to obtain clear and sharp images of the peripheral edges of the cornea, i.e., the outer section of the cornea that is still clear but which is adjacent the sclera. Obtain clear images of this portion of the cornea, as well as obtaining precise position and shape of this section of the cornea is beneficial, for example during cataract surgery. It is this section of the eye that the incision is made to provide access to the lens. Because this area of the cornea is clear it is difficult for convention technology, such as OCT, to obtain the clarity and sharpness of images necessary to precisely determine the position and shape of this area. In addition, the scanned illumination techniques enhance details in the anterior and posterior capsules and enables imaging of posterior capsule through dense cataracts.

Figure 7A:
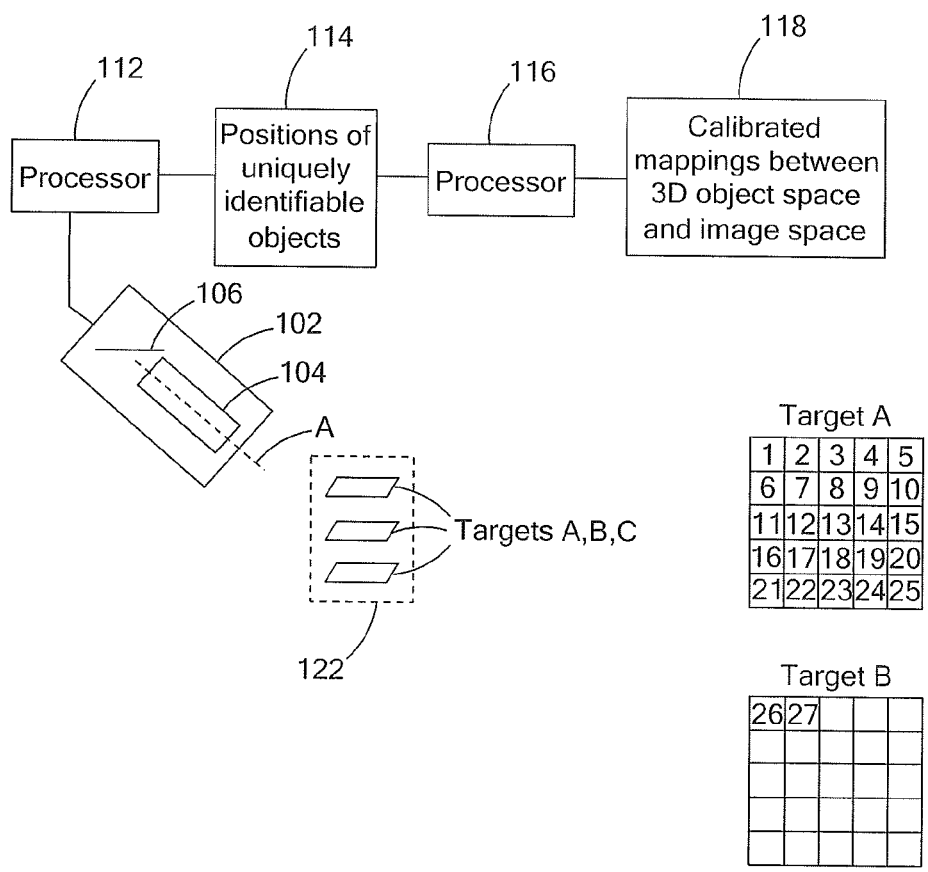
FIG. 7A schematically shows a portion of a system for calibrating images of an object, such as an eye, in accordance with the present invention.
Figure 7B:
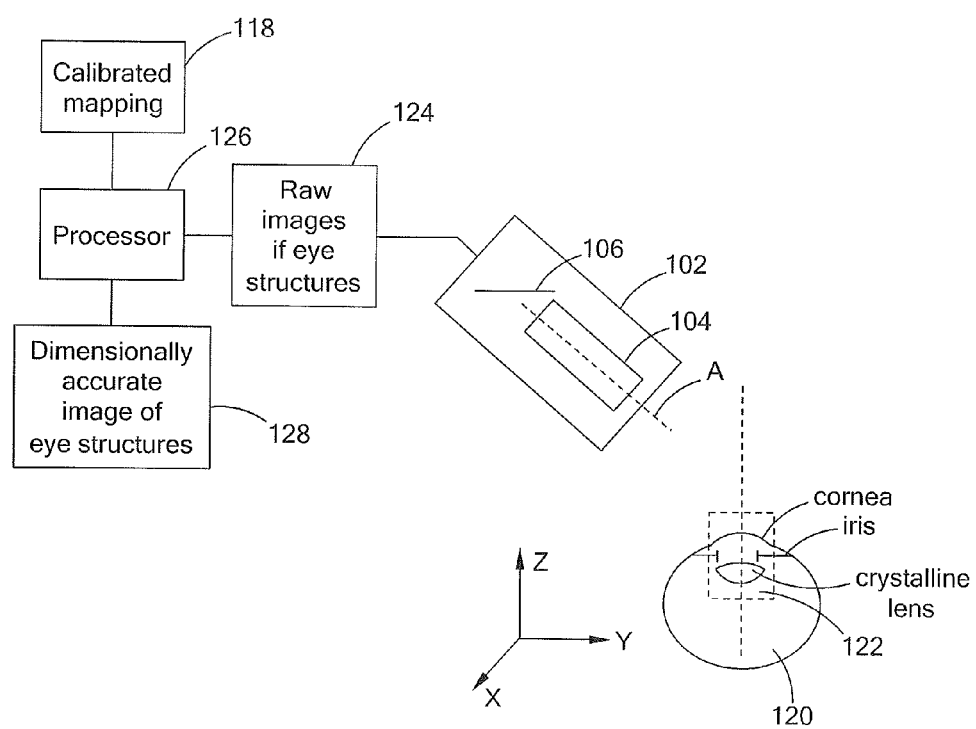
FIG. 7B schematically shows a second portion of the system of FIG. 7A in accordance with the present invention.

In order to correct for images generated in the systems and methods described previously with respect to FIGS. 1-6, a calibration procedure can be employed. As shown in FIGS. 7A-B, the calibration system 100 includes an image capture device 102, such as a camera, that including an image forming lens 104 and a planar detector 106 that has its plane angled relative to the optic axis A of the lens 104. An image receiving aperture 108 is aimed at an object volume 110, which contains the object of which the image capture device 102 forms an image. Such an arrangement, with an appropriately selected angle between the optic axis A of the lens 104 and the plane of the detector 106, allows the image capture device 102 to form an image with a large depth of focus in the z direction, which is aligned with the optic axis of the crystalline lens of an eye 120 as shown in FIG. 7B.

Referring to FIG. 7A, to calibrate the system, one or more targets, containing uniquely identifiable objects, such as squares 1, 2 . . . , are presented to the image capture device 102, usually sequentially. The targets are carefully made and are placed in exactly known positions. One example of such uniquely identifiable objects is ARTags as described in "Augmented Reality Tags", Augmented Reality: A Practical Guide, Stephen Cawood and Mark Fiala.

One or more images are generated for each target. The images formed at planar detector 106 are sent to processor 112, wherein processor 112 analyzes each image and identifies some or all of the uniquely identifiable objects in the image and records the positions of the uniquely identifiable objects in a memory 114. The recorded positions are then sent to processor 116, which generates a linear or non-linear mathematical relationship or mapping between the positions of the uniquely identifiable objects in the images of the targets and the accurately known positions of the uniquely identifiable objects within the object volume. An example of such a mapping is the TSAI algorithm. R. Y. Tsai, *An Efficient and Accurate Camera Calibration Technique for* 3*D Machine Vision*, Proceedings of IEEE Conference on Computer Vision and Pattern Recognition, Miami Beach, Fla., pp. 364-374, 1986.

The mapping is stored in memory 118 and is used to correct raw images generated by the image capture device to create dimensionally accurate images of the objects within the object volume. The use of uniquely identifiable objects greatly simplifies the process of generating the mathematical mapping required to create dimensionally accurate images.

The mapping determined above is used to process raw images of the structures within the eye, for example, surfaces and other features of the cornea and crystalline lens; c.f. FIG. 7B. As shown in FIG. 7B, the image capture device 102 forms raw images of the structures within the eye 120, which are situated in the object volume 122 and which are illuminated by a plane of light B which illuminates a longitudinal section of the eye 120. In FIG. 7B, the longitudinal section is perpendicular to the plane of the page. The raw images of the illuminated longitudinal section are subject to various sources of distortion including: the viewing angle between the optic axis of image capture device lens and the z axis, angle of the detector plane to the optic axis of the lens and optical aberrations in the image capture device lens. Accordingly, the raw images of the object volume 122 are stored in memory 124 and sent to processor 126. Using the calibrated mathematical mapping from memory 118, the processor 126 processes the raw images received from memory 124 to form substantially dimensionally accurate images of the eye that are stored in memory 128.

In other words, distances between structures or parts of structures measured on the processed images correspond, except for an overall scale factor to the corresponding distances in the illuminated longitudinal section of the eye.

The dimensionally accurate images allow the application of laser energy used in the treatment of cataracts to be accurately applied to specific areas within the eye, for example to cut a capsulotomy or to fragment the crystalline lens into pieces for easier removal in a cataract procedure.

With the above mentioned discussion of improved illumination and calibration, it is envisioned that such techniques could be applied to various imaging and beam placement systems. One example of such a system is presented herewith. For example, it is envisioned to apply the improved illumination and calibration to a system that uses a confocal system where the imaging and beam delivery systems are coaxial and share a common focus and optical pathway. Such a system would have no systematic errors between the imaging of the eye and the delivery of laser shots, such as femtosecond pulses. The imaging system could be based on the Scheimpflug principle so that a single image from the anterior cornea to the posterior capsule is captured resulting in enhanced depth of field. The scanning laser being such that it enhances contrast at important interfaces and, thus allows for anterior and posterior capsule-fragments to be closer to the posterior place due to the more accurate beam placement due to the present invention. A scanning beam camera and optics would be used to provide a high contrast to noise ratio. Such an imaging system would use three-dimensional reconstruction from ray tracing and so avoids two-dimensional stitching of multiple scans.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. An enhanced illumination system for providing enhanced illumination of components of a multi-component structure, the enhanced illumination system comprising:
   a. an illumination light source for providing an illumination beam;
   b. a scanner optically associated with the illumination light source for scanning the illumination beam;
   c. a control system, associated with the illumination light source and the scanner, whereby the enhanced illumination system is capable of delivering the illumination beam in illumination scan patterns to predetermined areas of the multi-component structure:
   d. a first predetermined illumination scan beam provides a first pattern, the first pattern having a predetermined first rate and first area, whereby the enhanced illumination system is capable of delivering the first predetermined illumination beam scan to the multi-component structure;
   e. a second predetermined illumination scan beam provides a second pattern, the second pattern having a predetermined second rate and second area, whereby the enhanced illumination system is capable of delivering the second predetermined illumination beam scan to the multi-component structure; wherein at least one of the second rate or area is different from the first rate or area;
   f. means for digitally capturing a first image generated by the first predetermined illumination scan beam;
   g. means for digitally capturing a second image generated by the second predetermined illumination scan beam; and,
   h. the means for digitally capturing the first image and the means for capturing the second image comprising a different portion of the same means.

2. The enhanced illumination system of claim 1, wherein the illumination light source is a super luminescent diode.

3. The enhanced illumination system of claim 1, wherein the illumination light source is a laser.

4. The enhanced illumination system of claim 1, wherein the means for digitally capturing the first and second images comprises a camera.

5. The enhanced illumination system of claim 1, wherein the means for digitally capturing the first image comprises a line of pixels.

6. The enhanced illumination system of claim 1, where the means for digitally capturing the first image comprises a first pixel, and the means for digitally capturing the second image comprises a second pixel, whereby the first and second pixels are different.

7. An enhanced imaging system for providing enhanced illumination of the structures of an eye, the system comprising:
   a. an illumination light source for providing an illumination beam;
   b. a scanner optically associated with the illumination light source for scanning the illumination beam;
   c. a control system, associated with the illumination light source and the scanner; whereby the enhanced imaging system is capable of delivering the illumination beam in illumination scan patterns to predetermined areas of the eye in the following patterns:
   d. a first predetermined illumination scan beam provides a first pattern, the first pattern having a predetermined first rate and first area, whereby the enhanced imaging system is capable of delivering the first predetermined illumination beam scan to the eye;
   e. a second predetermined illumination scan beam provides a second pattern, the second pattern having a predetermined second rate and second area; whereby the enhanced imaging system is capable of delivering the second predetermined illumination beam scan to the eye; wherein at least one of the second rate or area is different from the first rate or area;
   f. means for digitally capturing a first image generated by the first predetermined illumination scan beam;
   g. means for digitally capturing a second image generated by the second predetermined illumination scan beam; and,
   h. the means for digitally capturing the first image and the means for capturing the second image comprising a different portion of the same means.

8. The enhanced imaging system of claim 7, wherein the illumination light source is a super luminescent diode.

9. The enhanced imaging system of claim 7, wherein the illumination light source is a laser.

10. The enhanced imaging system of claim 7, wherein the means for digitally capturing the first and second images comprises a camera.

11. The enhanced imaging system of claim 7, wherein the means for digitally capturing the first image comprises a line of pixels.

12. The enhanced imaging system of claim 7, where the means for digitally capturing the first image comprises a first pixel, and the means for digitally capturing the second image comprises a second pixel, whereby the first and second pixels are different.

* * * * *